United States Patent
Schleppnik

[11] 3,942,761
[45] Mar. 9, 1976

[54] 4-(2'-NORBORNYL)-2-BUTANONES

[75] Inventor: Alfred A. Schleppnik, St. Louis, Mo.

[73] Assignee: Monsanto Company, St. Louis, Mo.

[22] Filed: Nov. 16, 1973

[21] Appl. No.: 416,541

Related U.S. Application Data

[63] Continuation-in-part of Ser. No. 103,878, Jan. 4, 1971, abandoned.

[52] U.S. Cl. .............................. 252/522; 260/586 G
[51] Int. Cl.² ...................... A61K 7/46; C11B 9/00
[58] Field of Search ......... 252/522; 260/586 A, 598

[56] References Cited
UNITED STATES PATENTS

| | | | |
|---|---|---|---|
| 3,716,498 | 2/1973 | Hall | 252/522 |
| 3,748,344 | 7/1973 | McCloud et al. | 252/522 |
| 3,780,109 | 12/1973 | Schleppnik | 260/598 |

FOREIGN PATENTS OR APPLICATIONS

| | | |
|---|---|---|
| 2,200,090 | 7/1972 | Germany |
| 2,200,091 | 7/1972 | Germany |
| 2,121,543 | 9/1972 | France |

Primary Examiner—Donald B. Moyer
Attorney, Agent, or Firm—Howard C. Stanley; J. E. Maurer; Neal E. Willis

[57] ABSTRACT

4-(2'-norbornyl)-2-butanones characterized by the structural formula

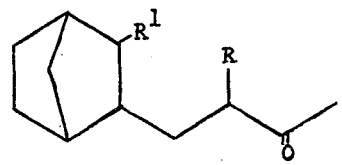

wherein $R^1$ represents hydrogen or methyl, and R represents hydrogen or a lower alkyl group are prepared by a crossed aldol condensation of 5-norbornene-2-carboxaldehyde or norbornane-2-carboxaldehyde with methyl ketones in a basic medium followed by a subsequent dehydration of the aldol formed to prepare the 3-buten-2-ones which are subsequently hydrogenated. The compounds have very pleasant, strong and long lasting woody odors and are useful as compounds in fragrance compositions.

4 Claims, No Drawings

4-(2'-NORBORNYL)-2-BUTANONES

This application is a continuation-in-part of my copending application, Ser. No. 103,878, filed Jan. 4, 1971, now abandoned.

This invention relates to the art of fragrance compositions and, more particularly, to a novel class of compounds possessing a characteristic odor. More specifically, this invention is directed to a novel class of useful compounds, their preparation and the utility of these compounds as fragrances.

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for new compounds possessing specific characteristic aromas.

In accordance with the present invention, there is provided a novel class of 4-(2'-norbornyl)-2-butanones. The compounds of this invention are prepared by a crossed aldol condensation of 5-norbornene-2-carboxaldehyde or norbornane-2-carboxaldehyde with methyl ketones in a basic medium followed by a subsequent dehydration of the aldol formed to prepare the 3-buten-2-ones which are subsequently hydrogenated. The class of compounds as a whole exhibits a characteristic pleasant, strong and long lasting aroma, which is highly useful in the preparation of fragrance compositions and perfumed products.

The principal object of the present invention is to provide a new class of aroma chemicals consisting of 4-(2'-norbornyl)-2-butanones and to methods of preparing them.

Another object of the present invention is to provide a specific class of norbornyl compounds having a characteristic aroma which is utilized in the preparation of fragrances and fragrance compositions.

These and other objects, aspects and advantages of this invention will become apparent from a consideration of the accompanying specification and claims.

In accordance with the above objects, there is provided by the present invention a novel class of compounds characterized by the structural formula

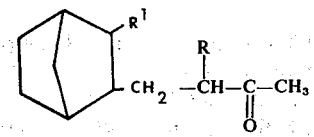

wherein $R^1$ represents hydrogen or methyl, and R represents hydrogen or a lower alkyl group, i.e., an alkyl group of from 1 to 8 carbon atoms.

Representative alkyl groups characterized by R in the above formula include methyl, ethyl, n-propyl, i-propyl, n-butyl, i-butyl, tert-butyl, n-amyl, tert-amyl, i-amyl, n-octyl and the like.

The novel compounds of this invention are prepared by reacting a 5-norbornene-2-carboxaldehyde or norbornane-2-carboxaldehyde characterized by the structure formula

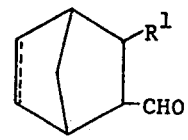

wherein $R^1$ is hydrogen or methyl, with a methyl ketone characterized by the structural formula

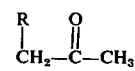

wherein R is hydrogen, lower alkyl or alkenyl of from 1 to 8 carbon atoms, in a basic medium. Such a reaction is illustrated by the following equation:

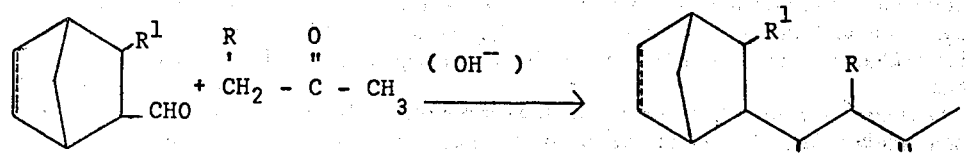

(I)

The resulting aldol is then dehydrated as illustrated in the following equation:

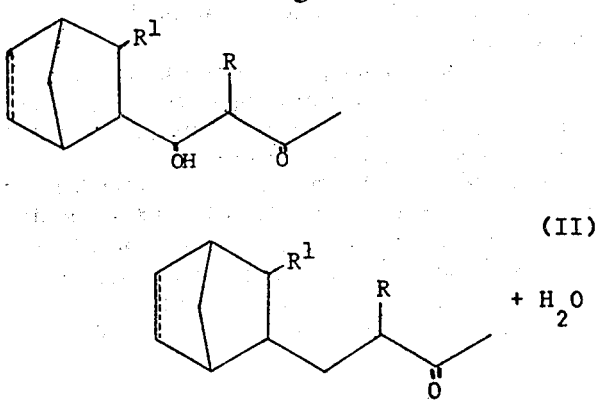

(II)

Although it has been found that a large portion of the aldol formed in equation (I) can be dehydrated by merely heating and maintaining the reaction mass at elevated temperatures, it is preferred to add a catalytic amount of a strong acid to more completely dehydrate all of the aldol formed. Illustrative of such acids are phosphoric acid, sulfuric acid, hydrochloric acid and the aryl sulfonic acids and the like.

The resulting 3-buten-2-ones are then hydrogenated to the 4-(2'-norbornyl)-2-butanones as illustrated in the following equation:

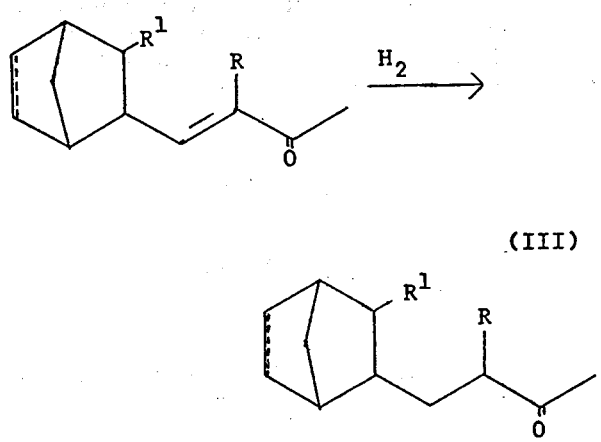

(III)

The methyl ketones described above include compounds such as acetone, 2-butanone, 2-pentanone, methyl isobutyl ketone, methyl amyl ketone, 6-methyl hept-5-en-2-one, allyl acetone 5-hexene-2-one and the like.

In a preferred embodiment of this invention, 5-norbornene-2-carboxaldehyde is reacted with methyl ethyl ketone in the presence of a strong base such as sodium hydroxide and the like. Alternatively, a strongly basic ion exchange resin may be used in lieu of the strong base.

Ordinarily the mixture of the norbornene or norbornane carboxaldehyde and the ketone is refluxed for varying lengths of time to afford the products of this invention. The reaction is preferably carried out in the presence of water and the lower alkanols.

The norbornene or norbornane carboxaldehydes and the ketones which are reacted in accordance with this invention are preferably reacted in a mole ratio of at least about 1 to 1, preferably about 1 to 2 and most preferred to about 1 to 5.

The strong bases can be the alkali and alkaline earth metal hydroxides as well as other materials that form basic mediums.

The reaction conditions are not critical but should be such as to facilitate the preparation of the products. Thus, the reaction is normally conducted at a temperature of from ambient temperatures up to about 120°C.

The novel compounds of this invention are useful in the preparation and formulation of fragrance compositions such as perfumes and perfumed products due to their pleasing, strong and long lasting aroma. Perfume compositions and the use thereof in cosmetic, detergent and bar soap formulations and the like are exemplary of the utility thereof.

The term "fragrance composition" as used herein refers to a composition that has the quality or state of having a sweet or delicate odor. As such, fragrance compositions of the instant invention comprise the instant compounds, in an odoriferous amount, and at least one other odoriferous compound.

The compounds of this invention are used in concentrations of from trace amounts up to about 50 percent of the perfume composition into which they are incorporated. As will be expected, the concentration will vary depending on the particular fragrance composition and even within the same composition when compounded by different perfumers.

The following examples will serve to illustrate certain specific embodiments within the scope of this invention and are not to be construed as limiting the scope thereof.

EXAMPLE 1

4-(5-Norbornenyl)-3-methyl-but-3-en-2-one

A mixture of 80 ml. of 2-butanone (1.1 moles), 61.1 grams (0.5 moles) of 5-norbornene-2-carboxaldehyde, and 250 ml. of water containing 6 ml. of 40% sodium hydroxide solution was stirred rapidly at 50°C. for 2 hours when most of the aldehyde had been consumed (as determined by infrared analysis) and an aldol had formed. Stirring was continued and the temperature was slowly raised to 70°C. and kept there for 30 minutes causing dehydration of 75% of the aldol. A small amount of toluene sulfonic acid was added which catalyzed the dehydration of the remaining aldol. 90.8 grams of crude material which was a viscous liquid was distilled through a short Vigreux-column to give 4-(5-norbornenyl)-3-methyl-but-3-en-2-one which had a boiling point of 121°–122°C. at 10 mm., $n_D^{25} = 1.5156$.

EXAMPLE 2

3-Methyl-4-(2'-norbornyl)-2-butanones

A solution of 28.2 grams of 4-(5-norbornenyl)-3-methylbut-3-en-2-one and 50 ml. of ethanol was hydrogenated over 1 gram 5% palladium on charcoal at 5 psi at room temperature. The resulting product was distilled through a short Vigreux-column to give 25.3 grams of 3-methyl-4-(2'-norbornyl)-2-butanone which had a boiling point of 108° to 113°C. at 10 mm., $n_D^{25} = 1.4711$ and was a colorless liquid.

EXAMPLE 3

An excellent hyacinth type fragrance composition was prepared containing the compound of Example 2.

This fragrance composition was prepared by blending the ingredients using conventional blending methods.

| Ingredient | Parts by Weight |
| --- | --- |
| phenyl acetic acid | 5 |
| ionone standard AB | 25 |
| linalool synthetic | 25 |
| iso eugenol | 25 |
| heliotropine recrystal | 50 |
| benzyl acetate | 50 |
| phenyl ethyl alcohol | 50 |
| benzyl alcohol | 100 |
| phenyl acid acetaldehyde dimethyl acetal | 170 |
| 3-methyl-4-(2'-norbornyl)-2-butanone | 1 |
| Hercolyn D* | 499 |

*trademarked fixative and diluent of the Hercules Company.

While this invention has been described hereinabove with regard to certain illustrative specific embodiments, it is not so limited since many modifications and variations are possible in the light of the above teachings. It is understood therefore that the invention may be practiced otherwise than as specifically described without departing from the spirit and scope of the invention.

The embodiments of this invention in which an exclusive property or privilege is claimed are defined as follows:

1. In the method of preparing a fragrance composition, the step comprising incorporating therein an odoriferous amount of a compound of the formula

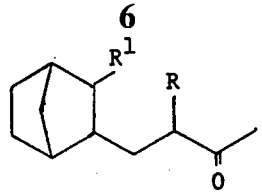

wherein $R^1$ is hydrogen or methyl and R is hydrogen or a lower alkyl group containing from 1 to 8 carbon atoms.

2. The method of claim 1 wherein the compound incorporated is 3-methyl-4-(2'-norbornyl)-2-butanone.

3. A fragrance composition having incorporated therein an odoriferous amount of a compound of the formula

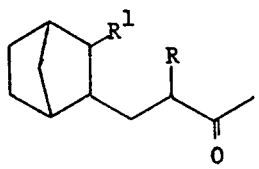

wherein $R^1$ is hydrogen or methyl and R is hydrogen or a lower alkyl group containing from 1 to 8 carbon atoms and at least one other odoriferous compound.

4. A fragrance composition of claim 3 wherein the compound that has been incorporated is 3-methyl-4-(2'-norbornyl)-2-butanone.

* * * * *